(12) United States Patent
Whitehurst et al.

(10) Patent No.: US 6,901,294 B1
(45) Date of Patent: May 31, 2005

(54) METHODS AND SYSTEMS FOR DIRECT ELECTRICAL CURRENT STIMULATION AS A THERAPY FOR PROSTATIC HYPERTROPHY

(75) Inventors: Todd K. Whitehurst, Frazier Park, CA (US); James P. McGivern, Stevenson Ranch, CA (US); Janusz A. Kuzma, Parker, CO (US)

(73) Assignee: Advanced Bionics Corporation, Valencia, CA (US)

( * ) Notice: Subject to any disclaimer, the term of this patent is extended or adjusted under 35 U.S.C. 154(b) by 110 days.

(21) Appl. No.: 10/133,771

(22) Filed: Apr. 26, 2002

Related U.S. Application Data
(60) Provisional application No. 60/293,808, filed on May 25, 2001.

(51) Int. Cl.[7] ................................................ A61N 1/08
(52) U.S. Cl. ........................................................ 607/39
(58) Field of Search ............................ 607/1, 2, 39–41, 607/50; 604/20, 21; 128/898, 899

(56) References Cited

U.S. PATENT DOCUMENTS

| | | | |
|---|---|---|---|
| 4,121,592 A | 10/1978 | Whalley | |
| 5,193,539 A | 3/1993 | Schulman et al. | |
| 5,193,540 A | 3/1993 | Schulman et al. | |
| 5,312,439 A | 5/1994 | Loeb | |
| 5,324,316 A | * 6/1994 | Schulman et al. | ............ 607/61 |
| 5,366,490 A | 11/1994 | Edwards et al. | |
| 5,529,574 A | 6/1996 | Frackelton | |
| 5,800,493 A | 9/1998 | Stevens et al. | |
| 5,919,187 A | 7/1999 | Guglielmi et al. | |
| 6,016,452 A | 1/2000 | Kasevich | |
| 6,021,347 A | 2/2000 | Herbst et al. | |
| 6,035,237 A | 3/2000 | Schulman et al. | |
| 6,051,017 A | 4/2000 | Loeb et al. | |
| 6,164,284 A | 12/2000 | Schulman et al. | |
| 6,177,404 B1 | * 1/2001 | DeFeo-Jones et al. | ......... 514/8 |
| 6,185,452 B1 | 2/2001 | Schulman et al. | |
| 6,190,381 B1 | 2/2001 | Olsen et al. | |
| 6,208,894 B1 | 3/2001 | Schulman et al. | |
| 6,296,639 B1 | 10/2001 | Truckai et al. | |
| 6,366,818 B1 | 4/2002 | Bolmsjo | |
| 6,472,991 B1 | 10/2002 | Schulman et al. | |
| 6,650,943 B1 | * 11/2003 | Whitehurst et al. | ........... 607/39 |
| 2002/0193859 A1 | 12/2002 | Schulman et al. | |

FOREIGN PATENT DOCUMENTS

| | | |
|---|---|---|
| WO | WO-97/02794 A1 | 1/1997 |
| WO | WO-98/43700 A1 | 10/1998 |
| WO | WO-98/43701 A1 | 10/1998 |

OTHER PUBLICATIONS

Ando, et al., "Treatment of Solid Tumor by a Direct Electric Current", Japanese Journal of Cancer and Chemotherapy, vol. 26(12), (Oct. 1999), pp. 1856–1859.

(Continued)

Primary Examiner—George Manuel
(74) Attorney, Agent, or Firm—Laura Haburay Bishop (57) ABSTRACT

A small implantable stimulator(s) includes at least two electrodes for delivering electrical stimulation to surrounding tissue. The small stimulator provides means of stimulating the prostate with direct electrical current, such as relatively low-level direct current, without the need for external appliances during the stimulation session. The stimulator may be configured to be small enough to be implanted entirely within the prostate. Open- and closed-loop systems are disclosed.

26 Claims, 6 Drawing Sheets

OTHER PUBLICATIONS

Berendson, et al., "Electrochemical Aspects of Treatment of Tissue with Direct Current", European Journal of Surgery, Suppl. 574, (1994), pp. 111–115.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781–790.

Griffin, et al., "Low–Level Direct Electrical Current Therapy for Hepatic Metastases. I. Preclinical Studies on Normal Liver", British Journal of Cancer, vol. 72(1), (Jul. 1995), pp. 31–34.

Plesnicar, et al., "Electric Treatment of Human Melanoma Skin Lesions with Low Level Direct Electric Current: An Assessment of Clinical Experience Following a Preliminary Study in Five Patients", European Journal of Surgery, Suppl. 574, (1994), pp. 45–49.

Shulman, et al., "Simultaneous Bilateral Obturator Nerve Stimulation During Transurethral Electrovaporization of the Prostate", J Clin Anesth, vol. 10(6), (Sep. 1998), pp. 518–521.

Taylor, et al., "Ablation of Neoplasia by Direct Current", British Journal of Cancer, vol. 70(2), (Aug. 1994), pp. 342–345.

Turler, et al., "Local Treatment of Hepatic Metastases with Low–Level Direct Electric Current: Experimental Results", Journal of Gastroenterology, vol. 35(3), (Mar. 2000), pp. 322–328.

Yen, et al., "Electrochemical Treatment of Human KB Cells in Vitro", Journal Bioelectromagnetics, vol. 20(1), (1999), pp. 24–41.

* cited by examiner

METHODS AND SYSTEMS FOR DIRECT ELECTRICAL CURRENT STIMULATION AS A THERAPY FOR PROSTATIC HYPERTROPHY

The present application claims the benefit of U.S. Provisional Patent Application Ser. No. 60/293,808, filed May 25, 2001, which application is incorporated herein by reference in its entirety.

FIELD OF THE INVENTION

The present Invention generally relates to implantable stimulator systems and methods, and more particularly relates to implantable stimulator systems and methods utilizing one or more implantable microstimulators for direct electrical current stimulation as a therapy for prostatic hypertrophy.

BACKGROUND OF THE INVENTION

The prostate gland, a key part of the male reproductive system, is linked closely with the urinary system. It is a small gland that secretes much of the liquid portion of the semen, the milky fluid that transports sperm through the penis when a man ejaculates. The prostate is located just beneath the bladder. It encircles, like a donut, a section of the urethra, which is the tube that carries urine from the bladder out through the penis. During ejaculation, semen is secreted by the prostate through small pores in the urethra's walls.

Benign Prostatic Hyperplasia (BPH) is an enlarged prostate. Benign means noncancerous and hyperplasia means excessive growth of tissue. BPH is the result of small noncancerous growths inside the prostate. It is not known what causes these growths, but they may be related to hormone changes that occur with aging. By age 60, more than half of all American men have microscopic signs of BPH, and by age 70, more than 40 percent have enlargement that can be felt on physical examination. The prostate normally starts out about the size of a walnut. By the time a man is age 40, the prostate may already have growth to the size of an apricot. By age 60, it may be as big as a lemon.

BPH, which does not affect sexual function, is nonetheless troublesome. As the prostate enlarges, it presses against the bladder and the urethra, blocking urine flow. A patient with BPH may find it difficult to initiate a urine stream or to maintain more than a dribble. He may also need to urinate frequently, or he may have a sudden, powerful urge to urinate. Many patients suffer from nocturia (i.e., they awaken several times a night to void); others suffer from urgency and frequency (e.g., an annoying feeling that the bladder is never completely empty).

Straining to empty the bladder can make matters worse—the bladder stretches, the bladder wall thickens and loses its elasticity and the bladder muscles become less efficient. The pool of urine that collects in the bladder can foster urinary tract infections, and trying to force a urine stream can produce back pressure that eventually damages the kidneys (a condition known as hydronephrosis).

BPH can lead to other problems. For Instance, a completely blocked urethra is an emergency requiring immediate catheterization (a procedure where a tube called a catheter is Inserted through the penis into the bladder to allow urine to escape). Other serious potential complications of BPH include bladder stones and bleeding.

About half of the men with BPH develop symptoms serious enough to warrant treatment. BPH cannot be cured, but in many cases, its symptoms are relieved by surgery or by drugs.

BPH Surgery

The popularity of prostate surgery has diminished since drug therapy became available: a total of 250,000 procedures were performed in 1996, down from 400,000 in 1988. Despite this, operations for BPH remain the most common surgery performed on American men. Several types of surgery can relieve the symptoms of an enlarged prostate.

Transurethral Resection of the Prostate (TURP): This procedure accounts for more than 90 percent of all BPH surgeries. TURP relieves symptoms quickly, typically doubling the urinary flow within weeks. This procedure typically proceeds as follows: The patient is numbed from the waist down with an anesthetic injection known as a spinal block. The surgeon then inserts a slim fiberscopic tube through the penis and up the urethra as far as the prostate. Using either a tiny blade or an electric loop, the surgeon pares away the urethra's lining and bits of excess prostate tissue. Gradually, the passageway is expanded.

The TURP procedure ordinarily does not pose the two main dangers generally linked to prostate surgery: incontinence (loss of urinary control) and problems with sexual function, especially sexual impotence (the inability to have an erection). About five percent of men become partially incontinent after the TURP procedure. In addition, some men develop scarring in the urethra, which can block urination. As many as 10 percent will need repeat surgery because prostate tissue grows back.

About five percent of men become impotent after the TURP procedure. But TURP does not usually affect a man's ability to have an erection or orgasm, since the nerves that control erection lie outside the prostate and are not touched by the operation. A more common side effect is a dry or retrograde ejaculation. The result is that semen spurts backward in to the bladder rather than through the penis. Men who experience this side effect still have the sensation of an orgasm but are unable to father children.

Transurethral Incision of the Prostate (TUIP): This procedure Is used in small prostate glands of 30 grams or less and is used far less frequently than TURP. Like TURP, TUIP is performed by passing an instrument through the penis to reach the prostate. The difference is that a doctor makes only one or two small cuts to relieve pressure in the prostate rather than trimming away tissue. Like TURP, the procedure considerably increases the urine flow. TUIP is an outpatient procedure with a low risk of side effects. Because of that, the United States Public Health Service Clinical Practice Guidelines recommend that this technique be used more often.

Transurethral Needle Ablation (TUNA): This technique, which can be done with a local anesthetic on an outpatient basis, uses radio frequency delivered through needles to kill excess prostate tissue. A catheter that deploys the needles toward the obstructing prostate tissue is inserted into the urethra before the procedure begins. Some clinical studies have reported that TUNA improves the urine flow with minimal side effects when compared with other procedures.

Open Prostatectomy: In this procedure, a surgeon makes an incision to reach the prostate, instead of inserting an instrument through the urethra. Open prostatectomy may involve either a radical or a partial procedure. A radical prostatectomy, which removes the whole prostate, is a treatment used for prostate cancer. The incision is made through either the lower abdomen or the perineum. Partial prostatectomy, which leaves the posterior portion of the prostate intact, is used to treat BPH. The incision for a partial prostatectomy is again made through either the lower abdomen or the perineum. Partial prostatectomy once was the sole recourse for an enlarged prostate. Today it is used only on extremely large prostates, which represent about five percent of all cases.

BPH Drug Therapy

Although regarded as less effective than surgery, drugs are also less invasive and usually free of major side effects. Currently two major classes of drugs are used for the treatment of BPH: alpha-adrenergic blockers and finasteride.

Alpha-adrenergic blockers were originally used for the treatment of high blood pressure, as they lead to relaxation of the smooth muscle in blood vessel walls. In BPH, they relax the muscular portion of the prostate and the bladder neck. This allows urine to flow more freely. In the average patient, these drugs increase the rate of urine flow and reduce symptoms, often within days. Side effects include dizziness, fatigue and headache.

Finasteride shrinks the prostate by blocking an enzyme that converts the male hormone testosterone into a more potent, growth-stimulating form. Some, but not all, studies show that taking finasteride for at least six months can increase urinary flow rate and reduce symptoms. It seems to work best for men who have greatly enlarged prostates. In a small percentage of men, the drug can affect sexual activity: decreasing a man's interest in sex, diminishing his ability to have an erection, and causing problems with ejaculation. It sometimes also causes tenderness or swelling of the breasts. It may cause a drop in PSA levels. (PSA is typically elevated in prostate cancer, and finasteride is used in the treatment of prostate cancer.) Stopping the drug typically reverses these side effects.

Other BPH Treatments

Researchers are working to develop BPH treatments that are more effective and less traumatic, with fewer side effects. These include using laser surgery, high amplitude electric currents, and microwaves. Some surgeons have also tried to enlarge the urethra by inserting a balloon into it and inflating it with fluid. Other surgeons have tried inserting a stent into the urethra to hold it open. Brachytherapy, in which "seeds" emitting low-level radiation are implanted in the prostate to kill the surrounding tissue, may also be used to shrink the volume of the prostate, but this treatment is typically reserved for prostate cancer. Transurethral electrovaporization of the prostate has been investigated for treatment of BPH. Electrovaporization is similar to traditional electrocautery; however, electrovaporization requires increased power.

Drawbacks of available BPH treatments include significant side effects, discomfort, inconvenience, and/or complex, risky, expensive surgical procedures, which may be confined to use in patients with severe symptoms and the capacity to finance the surgery. What is needed is an effective treatment for BPH that is minimally invasive, and provides relief without major side effects.

SUMMARY OF THE INVENTION

The invention disclosed and claimed herein addresses the above and other needs and provides implantable, minimally invasive systems and methods for chronically stimulating the prostate with low-level direct electrical current. A miniature implantable electrical stimulator capable of delivering a direct electric current, including a low-level direct electric current, may be implanted in the prostate via a minimal surgical procedure to treat benign prostatic hypertrophy (BPH). Low-level direct electrical stimulation of the prostate may provide significant therapeutic benefits in the treatment, control, and/or prevention of BPH through reduction in the volume of the prostate. Low-level direct electrical current will likely be effective in reducing prostate volume through localized destruction of prostate tissue.

A microstimulator, such as a stimulator similar to a Bionic Neuron (also referred to as a BION® microstimulator), capable of delivering a direct electric current, including a low-level direct electric current, may be implanted in the prostate via a minimal surgical procedure (e.g., via a small incision and through a cannula, endoscopically, etc.) to treat BPH. A single microstimulator may be implanted, or two or more microstimulators may be implanted to achieve direct electric current application to a larger region or for a longer period of time.

The implantable current generator capable of supplying direct current (DC) used with the present invention possesses one or more of the following properties, among other properties:

at least two electrodes for applying current to surrounding tissue;

electronic and/or mechanical components encapsulated in a hermetic package made from biocompatible material(s);

an electrical coil or the like for receiving energy and/or information inside the package, which receives power and/or data by, for instance, inductive or radio-frequency (RF) coupling to a transmitting coil placed outside the body, thus avoiding the need for electrical leads to connect devices to a central implanted or external controller;

means for receiving and/or transmitting signals via telemetry;

means for receiving and/or storing electrical power within the microstimulator; and a form factor making the microstimulator implantable via a minimal surgical procedure.

The length and/or shape of the microstimulator may be varied in order to deliver more effective treatment, e.g., to bring more electrode surface area in contact with prostate tissue, or to treat prostates of different shapes or sizes. For example, the microstimulator may be a thin cylindrical device with an electrode at each end, or may be a flat circular device with two or more electrodes distributed around its periphery, or may be a spherical device with two or more electrodes distributed on its surface, or may have any size and configuration suitable for the particular treatment and stimulation parameters.

A microstimulator may operate independently, or in a coordinated manner with other implanted microstimulators, other implanted devices, or with devices external to the patient's body. For instance, a microstimulator may incorporate sensor(s) for sensing a patients condition, which information may be used to control electrical parameters in a closed loop manner. The sensing and stimulating capabilities may be incorporated into a single microstimulator. Alternatively or additionally, a sensor(s) may communicate sensed information to at least one microstimulator with stimulation capabilities, i.e., that can supply a direct electric current.

BRIEF DESCRIPTION OF THE SEVERAL VIEWS OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
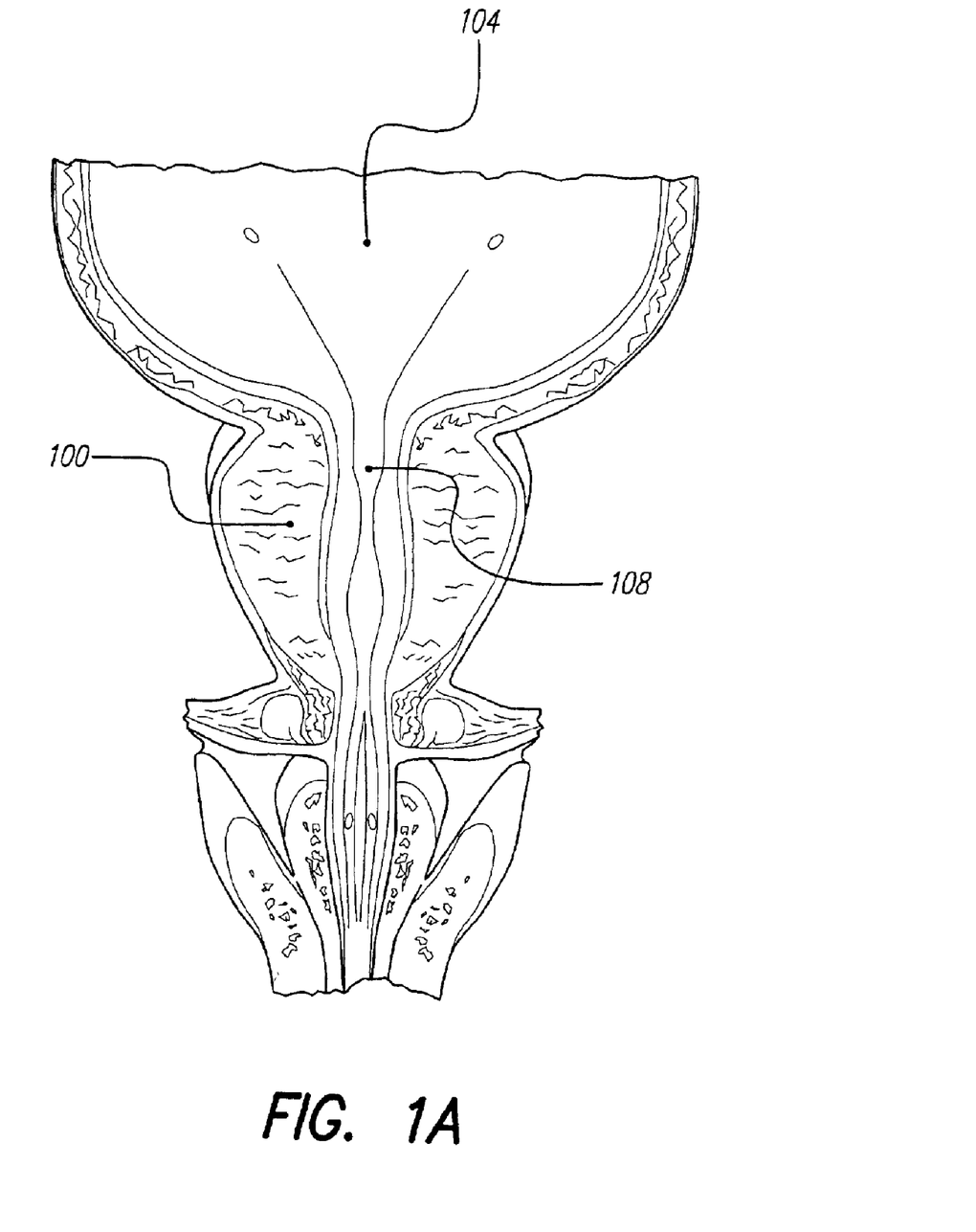
FIG. 1A is a frontal section view of the prostate gland, urethra, and surrounding tissues.
Figure 1B:
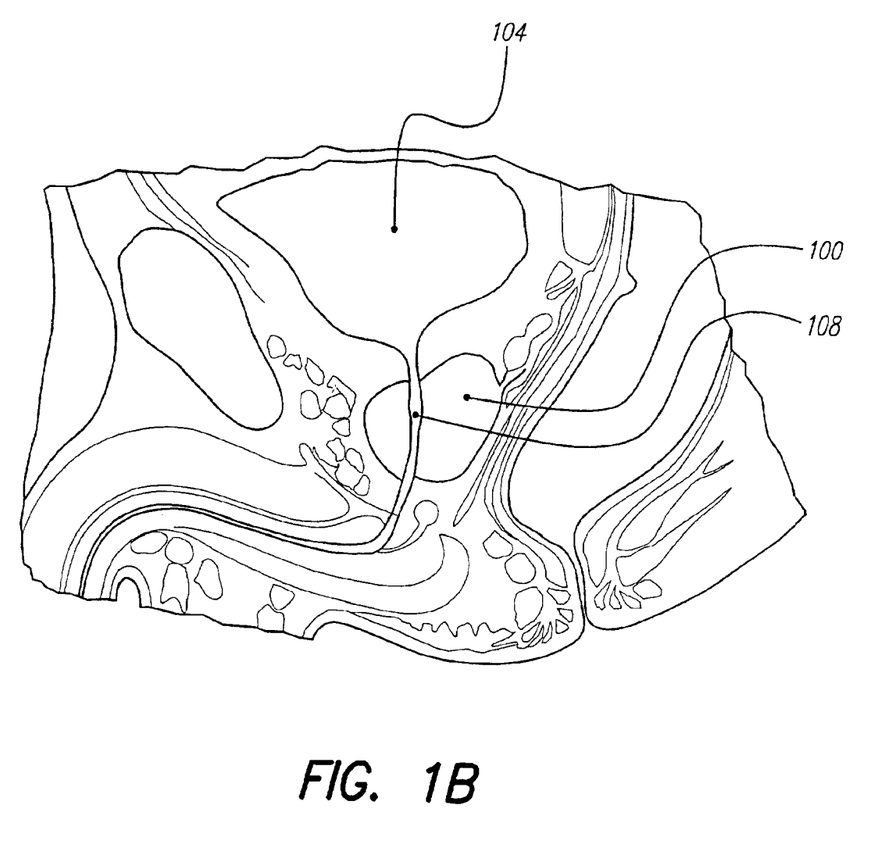
FIG. 1B is a sagittal section view of the prostate gland, urethra, and surrounding tissues.
Figure 2:
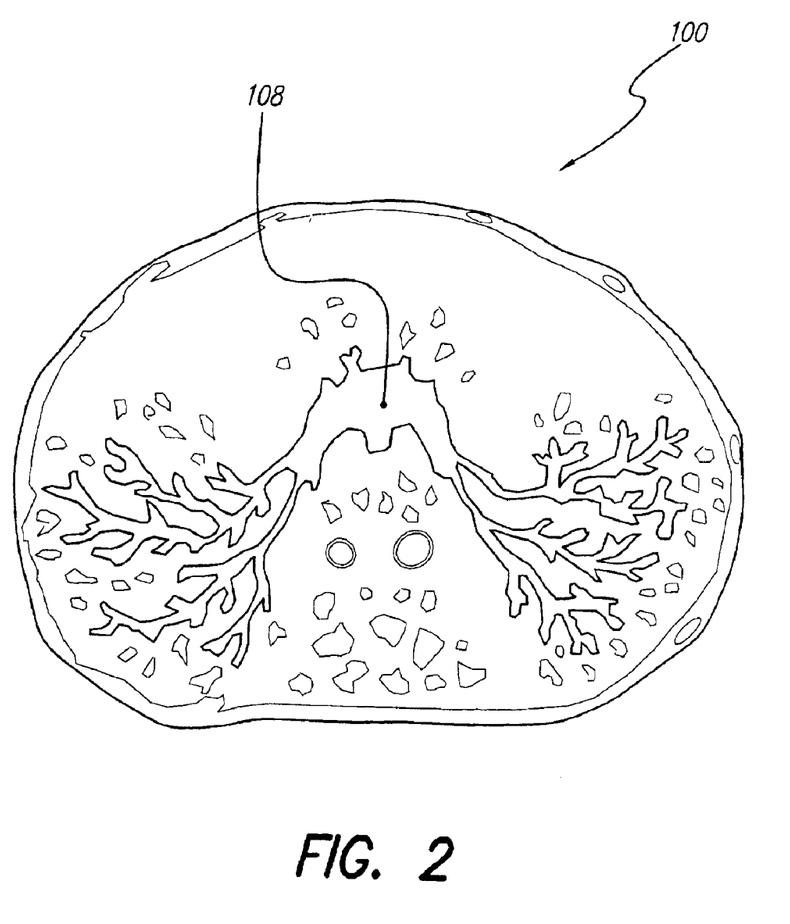
FIG. 2 depicts a cross-section through the prostate.

FIGS. 1A and 1B show a frontal section view and a sagittal section view, respectively, of the prostate gland, urethra, and surrounding tissues. FIG. 2 depicts a cross-section through the prostate. As can be seen, the prostate 100 is located just beneath the bladder 104, and the prostate 100 encircles the urethra 108. As described earlier, the prostate gland is a key part of the male reproductive system, and is closely linked with the urinary system.

Benign Prostatic Hyperplasia (BPH) is an enlarged prostate resulting from small, noncancerous growths inside the prostate. As prostate 100 enlarges, it presses against the bladder 104 and the urethra 108, hindering urine flow. As detailed earlier, a patient with BPH may have difficulty initiating and/or maintaining a urine stream, may need to urinate frequently, or may have a sudden, powerful urge to urinate. Additionally, many BPH patients suffer from nocturia (i.e., excessive urination at night).

Electrical Energy for Tissue Destruction

Low-level direct current (DC) electrical stimulation has been investigated as a means of tissue destruction, specifically as a treatment for cancer. It has various monikers in the medical literature, including direct electric current (DEC) therapy and electrochemical therapy (ECT).

A 1994 study described the primary reactions in the electrochemical treatment of tissue with direct electric current (Berendson, et al. "Electrochemical aspects of treatment of tissue with direct current." European Journal of Surgery, Suppl., 1994; (574):111–5). The main reactions at the anode are the formation of oxygen, acidification due to liberated hydrogen ions, and, if platinum is used as anode material, the formation of chloride. At the cathode, hydrogen is formed and hydroxide ions are liberated. Based on calculations, the authors concluded that the liberated hydrogen ions determine the extents of the locally destroyed zone around the anode and that the destructive effect of chlorine probably occurs in an inner zone close to the anode.

In an article published in the journal Bioelectromagnetics, titled "Electrochemical Treatment of Human KB Cells in Vitro" (1999; 20(1): 34–41), Yen, et al. reported applying a direct electric current of 400 $\mu$A at 3 volts for 62.5 minutes to a human cancer cell culture. This resulted in 1.5 Coulombs being delivered to 5 mL of culture medium, or 0.3 Coulombs/mL. This treatment was found to delay cell growth and decrease tumor cell survival. Interestingly, using higher current and a shorter treatment time resulted in better cell survival, indicating that chronic low-level stimulation may be more effective given the same amount of charge delivery. After treatment with 400 $\mu$A at 3 volts for 208.4 minutes (i.e., 5 Coulombs in 5 mL, or 1 Coulomb/mL), the pH at the anode decreased to 4.53 and increased to 10.46 at the cathode. The effect of pH alteration on cells is thus likely one of the mechanisms of tumor cell destruction.

In 1994, Taylor, et al. studied the application of low-voltage direct electrical current in animals and humans for the ablation of benign anal condylomata acuminata (i.e., anal warts), esophageal cancer, and Kaposi's sarcoma ("Ablation of neoplasia by direct current" British Journal of Cancer, 1994 August; 70(2):342–5). A direct electric current of 20 mA applied through multiple 6 cm×1 cm, flat-plate longitudinal electrodes into the squamous mucosa of the esophagus of healthy dogs for periods ranging from 10 minutes to 2 hours resulted in necrosis of the esophageal mucosa at the site of application of the current. In humans, the application of direct electrical current to two patients with benign anal condyloma acuminata, three patients with inoperable obstructing esophageal cancer, and one patient with disseminated Kaposi's sarcoma (a skin disease commonly afflicting AIDS patients) resulted in "striking necrosis of tumor tissue" that was confirmed by macroscopic and microscopic studies.

Also in 1994, Plesnicar, et al. investigated the effects of negative low-level direct electric current electrotherapy (with an electric current of 1 mA and a treatment time of 30 minutes) in metastatic or primary melanoma skin lesions ("Electric treatment of human melanoma skin lesions with low level direct electric current: an assessment of clinical experience following a preliminary study in five patients" European Journal of Surgery, Supplement, 1994; (574) :45–9). After 12 applications in five patients, tumor regression was observed in all melanoma skin lesions; four of them were classified as partial responses. No serious side effects were observed.

Turler et al., in the article "Local Treatment of Hepatic Metastases with Low-Level Direct Electric Current: Experimental Results" (published in the Scandanavian Journal of Gastroenterology, 2000 March; 35(3): 322–8), demonstrated that low-level direct current application is an effective modality for the treatment of hepatic metastases. Using an animal model with induced cancer metastasized to the liver, direct current (80 Coulombs/cm$^3$) was applied for five weeks in the treatment group by means of one anode in the tumor center and four cathodes peripherally. In the control group, electrodes were placed without applying current. After five weeks, magnetic resonance imaging (MRI) showed a 1.6-fold tumor enlargement in the treatment group, versus a 2.9-fold enlargement in the control group. Histopathologic analysis of the treated livers yielded a 21% complete response rate and a 78% partial response rate. No necroses were found in the control group.

In 1995, Griffin, et al.,also investigated the application of low-level direct electrical current to hepatic metastases in an animal model ("Low-Level Direct Electrical Current Therapy for Hepatic Metastases. I. Preclinical Studies on Normal Liver" in the British Journal of Cancer, 1995 July; 72(1): 31–4). The quantitative and qualitative relationships between electrode polarity, charge, and tissue necrosis was specifically examined. Two distinct regions of necrosis were Induced, distinguishable histologically and by MRI: (i) a cylindrical region of primary necrosis centered on the electrode, its volume directly proportional to the charge passed, but greater at the anode than cathode; and (ii) a wedge-shaped infarct, apex at the electrode and base extending to the liver edge. The extent of this infarct was again greater at the anode than the cathode, but showed a sigmoidal relationship with charge. These results indicate pH changes at the electrodes as likely mediators of tissue injury, but show also that significant distant ischemic injury can occur as a consequence of primary damage.

Finally, Ando, et al. ("Treatment of Solid Tumor by a Direct Electric Current" Japanese Journal of Cancer and Chemotherapy, 1999 October; 26(12):1856–9) reported a case of a 37-year-old Japanese female with laryngeal cancer (specifically, sarcoma), which was treated by direct electric current. The patient had a complete remission, sustained for 4 years at the time of the report. Ando, et al. further reported that clinical treatment of solid tumors with direct electric current has been performed in more than 8,000 cases with complete remission in 25% of all cases and partial remission in 50%. The mechanism of action of direct electric current, however, remains unclear.

Drawbacks of available BPH treatments include significant side effects, discomfort, inconvenience, and/or complex, risky, expensive surgical procedures, which may be confined to use in patients with severe symptoms and the capacity to finance the surgery. Recently, small, chronic, implantable microstimulators have been introduced that can be implanted into soft tissues via a minimal surgical procedure. What is needed and provided herein is an effective treatment for BPH that uses such a chronic device(s), that is minimally invasive, and provides relief without major side effects.

In accordance with the teachings of the present invention and as discussed in more detail presently, direct electrical current, such as a low-level direct electrical current, delivered to the prostate 100 is provided to treat, control, and/or prevent BPH. Low-level direct electrical current will likely be effective in reducing prostate volume through localized destruction of prostatic tissue.

The present invention is directed to providing the treatment described herein using one or more small, implantable, electrical stimulators, referred to herein as "microstimulators". As used herein, stimulation refers to supplying a direct electrical current, including a low-level direct electrical current. Thus a stimulator or microstimulator is sometimes referred to herein as simply a stimulator, or as a current generator, and electrical current parameters are sometimes referred to herein as stimulation parameters.

The microstimulators of the present invention may be similar to or of the type referred to as BION® devices. The following documents describe various details associated with the manufacture, operation, and use of BION implantable microstimulators, and are all incorporated herein by reference:

| Application/Patent/ Publication No. | Filing/Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued June 28, 1994 | Implantable Microstimulator |
| U.S. Pat. No. 5,405,367 | Issued Apr. 11, 1995 | Structure and Method of Manufacture of an Implantable Microstimulator |

-continued

| Application/Patent/ Publication No. | Filing/Publication Date | Title |
| --- | --- | --- |
| PCT Publication WO 98/37926 | Published Sep. 3, 1998 | Battery-Powered Patient Implantable Device |
| PCT Publication WO 98/43700 | Published Oct. 8, 1998 | System of Implantable Devices For Monitoring and/or Affecting Body Parameters |
| PCT Publication WO 98/43701 | Published Oct. 8, 1998 | System of Implantable Devices For Monitoring and/or Affecting Body Parameters |
| U.S. Pat. No. 6,051,017 | Issued Apr. 18, 2000 | Improved Implantable Microstimulator and Systems Employing Same |
| | Published September 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

As will be evident to those of ordinary skill in the art upon review of the present description and of the publications listed above, the direct current (DC) blocking capacitor normally present in the circuitry of BIONs used for neurostimulation applications is removed when it is desired that the BIONs produce DC current where such current is a desired therapeutic modality, as in embodiments of the present invention.

Figure 3:
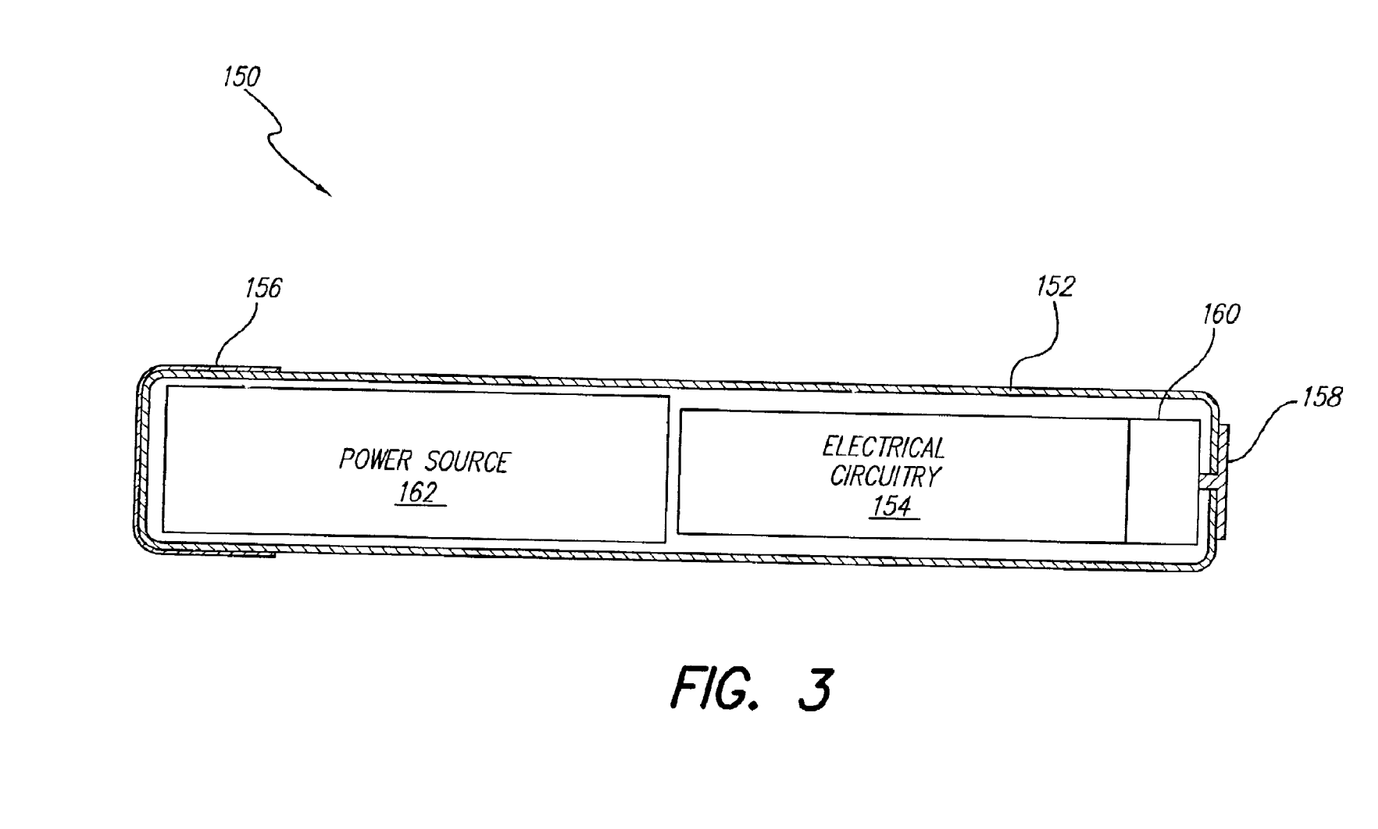
FIG. 3 is a side cross-sectional view of an exemplary embodiment of a stimulation system of the present invention.

As shown in FIG. 3, microstimulator device 150 may include a narrow, elongated capsule 152 containing electrical circuitry 154 connected to electrodes 156 and 158, which may pass through the walls of the capsule at either end. Alternatively, electrodes 156 and/or 158 may be built into and/or onto the case and/or arranged at the distal portion of a lead, as described below. As detailed in the referenced publications, electrodes 156 and 158 generally comprise a stimulating electrode (to be placed close to the target tissue) and an indifferent electrode (for completing the circuit). Other configurations of device 150 are possible, as is evident from the above-referenced publications, and as described in more detail herein.

Certain configurations of implantable microstimulator 150 are sufficiently small to permit placement entirely within or near prostate 100. In accordance with the present invention, a single microstimulator 150 may be implanted, or two or more microstimulators may be implanted to achieve direct electric current application to a larger region within the prostate or for a longer period of time, as discussed in more detail presently.

For instance, in some such configurations, capsule 152 may have a diameter of about 4–5 mm, or only about 3 mm, or even less than about 3 mm. In these configurations, capsule length may be about 25–35 mm, or only about 20–25 mm, or even less than about 20 mm. The shape of the microstimulator may be determined by the structure of the desired target, the surrounding area, and the method of implantation. A thin, elongated cylinder with electrodes at the ends, as shown in FIG. 3, is one possible configuration, but other shapes, such as rounded cylinders, disks, spheres, and helical structures, are possible, as are different configurations of and/or additional electrodes and/or leads.

In certain embodiments of the instant invention, microstimulator 150 comprises two, leadless electrodes. However, either or both electrodes 156 and 158 (or any of the electrodes, when more than two are used) may alternatively be located at the distal portion of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the bulk of the implantable stimulator 150, while allowing most elements of stimulator 150 to be located in a more convenient site. This minimizes the distance traversed and the surgical planes crossed by the device and any lead(s). In most uses of this invention, the leads are no longer than about 150 mm, so that stimulator 150, including leads and electrodes, is contained entirely within prostate 100, or is located nearby. As described herein, placement entirely within or near prostate 100 includes placement of a microstimulator with, for instance, an anode located in prostate 100 while a cathode (which electrode may be the microstimulator capsule itself) is located outside but close to the prostate, placement of the microstimulator with an anode and cathode located within prostate 100 while the bulk of the microstimulator is located outside but close to the prostate, and other similar arrangements that provide the benefits of the disclosed therapy.

In addition, the length and/or shape of the microstimulator may be varied in order to deliver more effective treatment, e.g., to bring more electrode surface area in contact with prostate tissue, or to treat prostates of different shapes or sizes. For example, if the microstimulator is a thin cylindrical device with an electrode at each end, the length of this device may be varied to treat prostates of different sizes. As another example, if the microstimulator is a flat circular (i.e., pancake-shaped) stimulator device with two or more electrodes distributed around its periphery, the diameter of this device may be varied to treat prostates of different sizes. As yet another example, a substantially spherical device with two or more electrodes distributed on its surface may have any size and configuration suitable for the particular treatment and stimulation parameters.

Microstimulator(s) 150, when certain configurations are used, may be implanted with a surgical tool such as a tool specially designed for the purpose, or may be placed, for instance, via a small incision and through a small cannula. Alternatively, device(s) 150 may be implanted via conventional surgical methods, or may be implanted using other endoscopic or laparoscopic techniques. A more complicated surgical procedure may be required for sufficient access to certain tissue, for fixing the microstimulator in place, and/or when implanting microstimulators of certain shapes.

The external surfaces of stimulator 150 may advantageously be composed of biocompatible materials. Capsule 152 may be made of, for instance, glass, ceramic or other material that provides a hermetic package that will exclude water vapor but permit passage of electromagnetic fields used to transmit data and/or power. Electrodes 156 and 158 may be made of a noble or refractory metal or compound, such as platinum, iridium, tantalum, titanium, titanium nitride, niobium, or alloys of any of these, in order to avoid corrosion or electrolysis which could damage the surrounding tissues and/or the device.

Microstimulator 150 contains, when necessary and/or desired, electrical circuitry 154 for receiving data and/or power from outside the body by inductive, radio frequency (RF), or other electromagnetic coupling. In some embodiments, electrical circuitry 154 includes an inductive coil or other means for receiving and transmitting RF data and/or power, an integrated circuit (IC) chip for decoding and storing stimulation parameters and generating stimulation current, and additional discrete electronic I components required to complete the electronic circuit functions, e.g. capacitor(s), resistor(s), coil(s), and the like.

Microstimulator 150 also includes, when necessary and/or desired, a programmable memory 160 for storing a set(s) of data, stimulation, control parameters, and/or other data, if required. Among other things, memory 160 may allow electrical and/or control parameters to be adjusted to settings that are safe and efficacious with minimal discomfort for each individual. Specific parameters may provide therapy for various forms and severity of BPH. For instance, some patients may respond favorably to intermittent stimulation, while others may require continuous stimulation to alleviate their symptoms.

In addition, different stimulation parameters may have different effects on prostatic tissue. For example, decades ago, research demonstrated that monophasic waveforms are toxic to neurons, due to the build-up of charge and associated pH change in the neurons. Since then, to avoid destroying neurons, biphasic pulses have typically been used for non-toxic electrical stimulation of tissue, e.g., neurostimulation, because the second phase reverses the charge injection and effectively removes the charge from the neuron. However, in the current invention, localized destruction of prostatic tissue via low-level direct electrical current will likely be effective in reducing prostatic volume. The volume of prostatic necrosis is likely to increase with an increasing amount of charge delivered to the tissue. In addition, a relatively lower amplitude direct electric current applied over a relatively longer treatment period may be more effective than a relatively higher amplitude direct electric current applied over a relatively shorter treatment period, even if the two treatments deliver the same amount of charge to the tissue.

In some embodiments of the current invention, electrical and control parameters are chosen to target specific tissues and to exclude others. For example, relatively low-level DC currents, e.g., less than about 100–500 $\mu A$, are likely to affect tissues very near the electrodes, i.e., within about a 3–4 mm radius of the electrode. Such low-level DC current may be less likely to damage vascular structures since the regular flow of blood through such structures rapidly removes toxic products, such as those created by DC currents, before they build to damaging levels.

Some embodiments of implantable current generator 150 also include a power source and/or power storage device 162. Possible power options for a current generator device of the present invention, described in more detail below, include but are not limited to an external power source coupled to current generator 150, e.g., via an RF link; a self-contained power source utilizing any suitable means of generation and/or storage of energy (e.g., a primary battery, a replenishable or rechargeable battery such as a lithium ion battery, an electrolytic capacitor, a super- or ultra-capacitor, or the like); and/or if the self-contained power source is replenishable or rechargeable, means of replenishing or recharging the power source (e.g., an RF link, an optical link, a thermal link, or other energy-coupling link).

Figure 4:
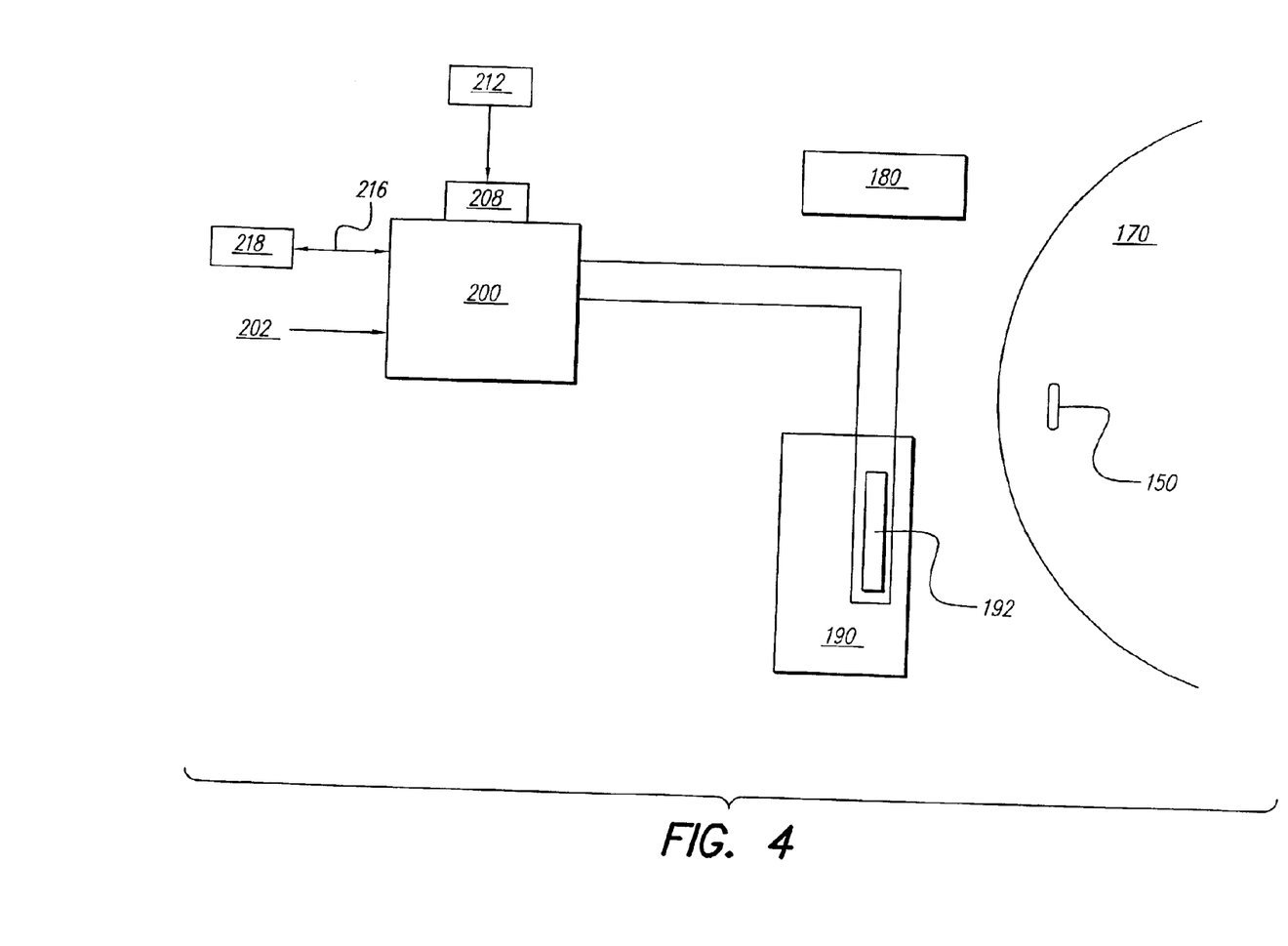
FIG. 4 illustrates exemplary external components of the invention.

In certain embodiments, and as illustrated in the exemplary embodiment of FIG. 4, the patient 170 switches stimulator 150 on and off by use of controller 180, which may be handheld. Controller 180 operates to control stimulator 150 by any of a variety of methods, including sensing the proximity of a permanent magnet located in controller 180, sensing RF transmissions from controller 180, or the like. Other methods for controlling microstimulator 150 are possible, such as an Implanted button that may be pressed to activate stimulator 150.

The embodiment of FIG. 4 also depicts exemplary external components related to programming and providing power to implantable stimulator 150. When it is required to communicate with implanted current generator 150, patient 170 is positioned on or near external appliance 190, which appliance contains one or more inductive coils 192 or other means of communication (e.g., RF transmitter and receiver). External appliance 190 is connected to or is a part of external electronic circuitry appliance 200 which may receive power 202 from a conventional power source. External appliance 200 contains manual input device 208, e.g., a keypad, whereby the patient 170 or a caregiver 212 may request changes in stimulation parameters produced during the normal operation of implantable stimulator 150. In these embodiments, manual input device 208 may include various electromechanical switches and/or visual display devices that provide the patient and/or caregiver with information about the status and prior programming of implantable stimulator 150.

Alternatively or additionally, external electronic appliance 200 is provided with an interface 216 for interacting with other computing device(s) 218, such as by a serial interface cable or infrared link to a personal computer, to a telephone modem, or the like. Such interface 216 may permit a clinician to monitor the status of the implant and prescribe new stimulation parameters from a remote location.

The external appliance(s) may be embedded In a cushion, pillow, mattress cover, or garment Other possibilities exist, Including a belt, patch, or other structure(s) that may be affixed to the patient's body or clothing. External appliances may include a package that can be, e.g., worn on the belt, may include an extension to a transmission coil affixed to the body, e.g., with a velcro band or adhesive, or may be combinations of these or other structures able to perform the functions described herein.

In order to help determine the strength and/or duration of electrical current required to produce the desired effect, in some embodiments, a patient's response to and/or need for treatment is sensed. For example, microstimulator 150 may incorporate means of sensing tissue necrosis or byproducts thereof (e.g., via a pH sensor or electrical impedance measurement), means of sensing tissue volume or indirect indicators thereof (e.g., via a pressure sensor), means of sensing tissue inflammation (e.g., electrical impedance measurement), and/or means of sensing tissue function or indirect indicators thereof (e.g., electromyograph or EMG). Other measures of the state of the patient may additionally or alternatively be sensed, e.g., hormone, enzyme, interleukin, cytokine, lymphokine, chemokine, growth factor, neurotransmitter, ketone, electrolyte, medication or other drug levels and/or changes In these or other substances in the blood plasma or local interstitial fluid. For instance, the level or changes in level of prostate specific antigen (PSA), a possible indicator of prostatic hypertrophy, may be sensed. Substances may be sensed, for instance, using one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands).

A microstimulator may additionally or alternatively incorporate means of sensing electrical current levels supplied by another source of electrical energy. For instance, multiple microstimulators may be placed in a patient, and one stimulator may modulate its output based on the current supplied by other microstimulators. Other methods of determining a patient's response to and/or need for treatment include an iterative process whereby the physician sets the current level and then adjusts it periodically based on diagnostic imaging results and/or a patient's report of symptoms, as well as other methods mentioned herein, and yet others that will be evident to those of skill in the art upon review of the present disclosure.

For instance, in several embodiments of the present invention, a first and second "microstimulator" are provided. The second "microstimulator" periodically (e.g., once per minute) records pH (or impedance, or other indicator), which it transmits to the first stimulator. The first stimulator uses the sensed information to adjust parameters according to an algorithm programmed, e.g., by a physician. For example, if pH is close to a predetermined physiological baseline (e.g., approximately 7.4), then the current is increased. In some alternatives, one "microstimulator" performs both the sensing and current generating functions, as discussed in more detail herein.

While a microstimulator may also incorporate means of sensing one or more conditions of the patient, e.g., via PSA or pH, it may alternatively or additionally be desirable to use a separate or specialized implantable device, such as an implantable pH sensor, to sense and telemeter physiological conditions/responses in order to adjust stimulation parameters. This information may be transmitted to an external device, such as external appliance 190, or may be transmitted directly to implanted stimulator(s) 150. However, in some cases, it may not be necessary or desired to include a sensing function or device, in which case stimulation parameters may be fixed and/or determined and refined, for instance, by patient feedback, or the like.

Thus, it is seen that in accordance with the present invention, one or more external appliances may be provided to interact with microstimulator 150, and may be used to accomplish, potentially among other things, one or more of the following functions:

Function 1: If necessary, transmit electrical power from the external electronic appliance 200 via appliance 190 to stimulator 150 in order to power the device and/or recharge the power source/storage device 162. External electronic appliance 200 may include an automatic algorithm that adjusts stimulation parameters automatically whenever the implantable stimulator(s) 150 is/are recharged.

Function 2: Transmit data from the external appliance 200 via the external appliance 190 to implantable stimulator 150 in order to change the operational parameters (e.g., electrical stimulation parameters) of stimulator 150.

Function 3: Transmit sensed data indicating a need for treatment or in response to stimulation from microstimulator 150 (e.g., EMG, change in pH, impedance, PSA, hormone, or medication level, or other activity) to external appliance 200 via external appliance 190.

Function 4: Transmit data indicating state of implantable stimulator 150 (e.g., battery level, stimulation parameters, etc.) to external appliance 200 via external appliance 190.

By way of example, a treatment modality for BPH may be carried out according to the following sequence of procedures:

1. A stimulator 150 is implanted so that it is entirely within prostate gland 100. If necessary or desired, one or more additional stimulator(s) 150 may be implanted in other areas of prostate 100. In another alternative, electrodes 156 and/or 158 are implanted in the prostate while the bulk of the stimulator is implanted a short distance away, near the prostate, e.g., in the abdomen.
2. Using Function 2 described above (i.e., transmitting data) of external appliance 200 and external appliance 190, stimulator 150 is commanded to produce continuous low-level DC electric current, e.g., at 100 $\mu$A.

3. Set stimulator on/off period(s) to an appropriate setting(s), e.g., one hour on then one hour off.
4. At some predefined interval, any change in pH, impedance, oxygen level, and/or PSA is sensed, for instance, by one or more electrodes 156 and 158 or sensors. These responses are converted to data and telemetered out to external electronic appliance 200 via Function 3. Alternatively, after an initial treatment period (e.g., one month), prostate size/state may be assessed by, for example, direct digital exam, report of BPH symptoms, ultrasound imaging, CT imaging, and/or other diagnostic Imaging.
5. From the response data received at external appliance 200 from implantable stimulator 150, or from other assessment, the DC current necessary to obtain a response is determined and is used by a clinician acting directly 212 or by other computing device 218 to transmit the desired DC current parameters to stimulator 150 in accordance with Function 2. For Instance, the DC current setting may be increased or decreased and/or the on/off periods may be adjusted. Increasing DC current or stimulator on period and/or decreasing stimulator off period is likely to increase tissue degradation and/or to further slow tissue growth.
6. To cease electrical current, patient 170 employs controller 180 to turn off stimulator 150.
7. Periodically, the patient or caregiver recharges the power source/storage device 162 of implantable stimulator 150, if necessary, in accordance with Function 1 described above (i.e., transmit electrical power).

For the treatment of any of the various forms and degrees of BPH, it may be desirable to modify or adjust the algorithmic functions performed by the implanted and/or external components, as well as surgical approaches, in ways obvious to skilled practitioners of these arts. For example, in some situations, it may be desirable to employ more than one implantable stimulator 150, each of which could be separately controlled, e.g., by a digital address. Multiple channels and/or multiple patterns of stimulation might thereby be programmed by the clinician and controlled by the patient to, for instance, stimulate larger areas of the prostate in order to maximize therapeutic efficacy.

Figure 5:
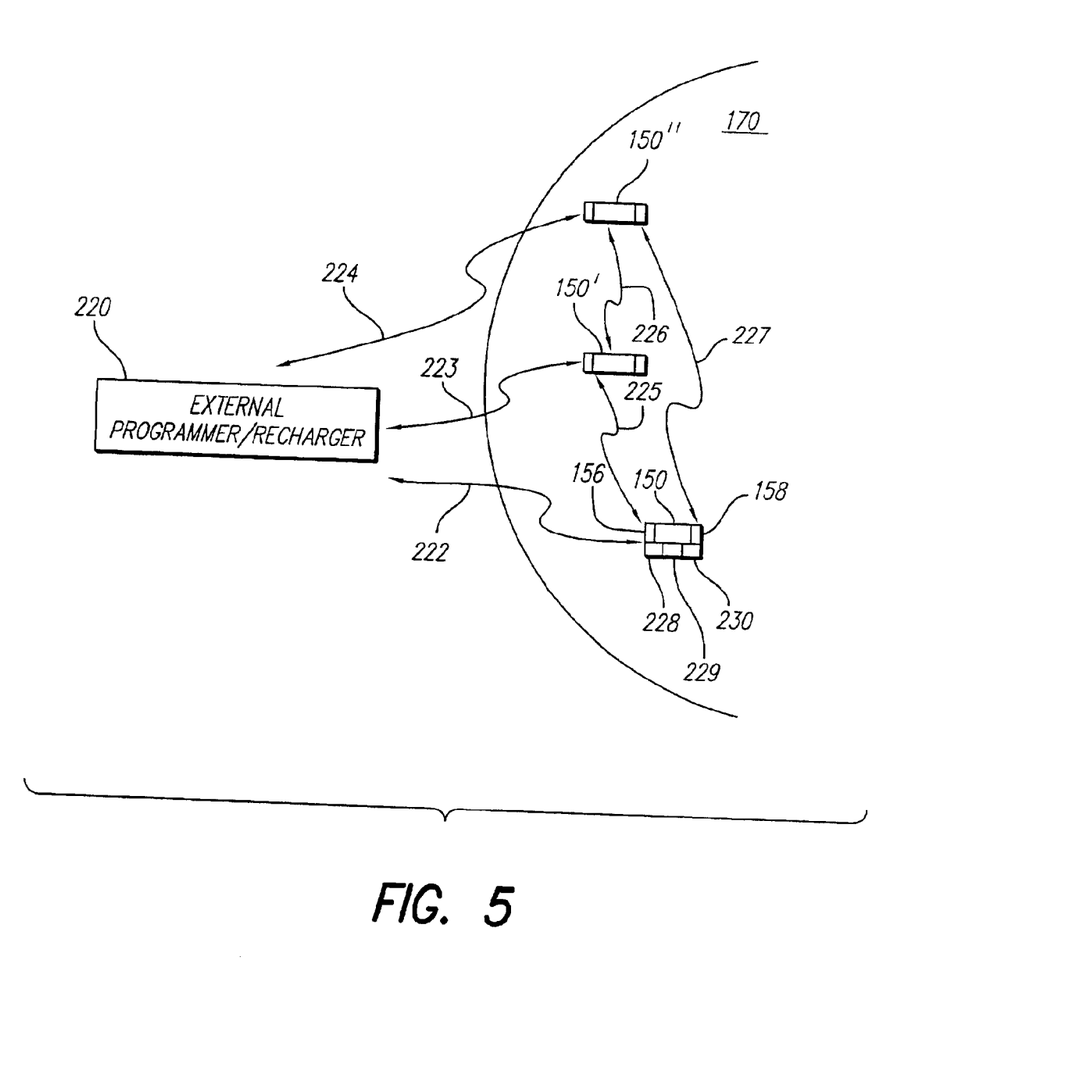
FIG. 5 depicts a system of implantable devices that communicate with each other and/or with external control/programming devices.

In some embodiments, microstimulator 150, or a group of two or more microstimulators, is controlled via closed-loop operation. A need for and/or response to stimulation is sensed via microstimulator 150, or by an additional microstimulator (which may or may not be dedicated to the sensing function), or by another implanted or external device. If necessary, the sensed information is transmitted to microstimulator 150. In some embodiments, the stimulation parameters used by microstimulator 150 are automatically adjusted based on the sensed information. Thus, the stimulation parameters may be adjusted in a dosed-loop manner to provide stimulation tailored to the need for and/or response to stimulation.

For instance, as shown in the example of FIG. 5, microstimulator 150, implanted beneath the skin 171 of the patient 170, provides electrical stimulation via electrodes 156 and 158 to a first location; a second microstimulator 150' provides electrical stimulation to a second location; and a third microstimulator 150" provides electrical stimulation to a third location. As mentioned earlier, the implanted devices may operate independently or may operate in a coordinated manner with other similar implanted device(s), other implanted device(s), and/or other device(s) external to the patient's body, as shown by control lines 222, 223, 224, 225, 226, and 227 in FIG. 5.

That is, in accordance with various embodiments of the invention, external controller(s) 220 control the operation of each implanted device (e.g., stimulators 150, 150' and 150"). According to certain embodiments, an implanted device, e.g. stimulator 150, may control or operate under the control of other implanted device(s), e.g., stimulator 150' and/or 150", or device(s) external to the patent's body, e.g., controller 220. A microstimulator made in accordance with the invention may communicate with other implanted microstimulators, other implanted devices, and/or external devices, e.g., via an RF link, an ultrasonic link, a thermal link, an optical link, or other communications link. Specifically, as illustrated in FIG. 5, microstimulator 150, 150', and/or 150", made in accordance with the invention, may communicate with an external remote control (e.g., patient and/or physician programmer 220) that is capable of sending commands and/or data to implanted device(s) and that may also be capable of receiving commands and/or data from implanted device(s).

A microstimulator made in accordance with certain embodiments of the invention further incorporates a first sensor 228 for sensing therapeutic effects, clinical variables, and/or other indicators of the state of the patient, such as PSA, pH, oxygen level, pressure, EMG, impedance, or the like. The stimulator may additionally or alternatively incorporate a second sensor 229 (e.g., a CHEMFET) for sensing level(s) and/or change(s) in one or more medications, other drugs, hormones, enzymes, interleukins, cytokines, lymphokines, chemokines, growth factors, neurotransmitters, ketones, electrolytes and/or other substances in the blood plasma or local interstitial fluid. The stimulator may additionally or alternatively incorporate a third sensor 230 for sensing electrical current levels and/or waveforms supplied by another source of electrical energy. Sensed information may be used to control parameters in a closed-loop manner, as shown by control lines 226, 227, and 225. Thus, sensor(s) may be incorporated into a device that also includes electrical stimulation, or the sensor(s) (that may or may not include stimulation capabilities) may communicate the sensed information to another device(s) with stimulation capabilities. In a further alternative, one or more of the sensors may also be a stimulating electrode or other electrode. If necessary, the sensed information is transmitted to an external device, which may process the information and communicate the needed information to other internal devices providing stimulation, as shown by control lines 222, 223, and 224.

According to various embodiments of the invention, sensing and electrical stimulation are both incorporated into a single microstimulator. According to various embodiments of the invention, the sensor(s) are incorporated into at least one "microstimulator" (that may or may not be capable of stimulating), and the sensed information is, if desired, communicated to at least one other microstimulator capable of stimulating, i.e., capable of supplying a direct electric current. The implant circuitry 154 may, if necessary, amplify and transmit these sensed signals, which may be analog or digital. Information sensed by the sensor(s) may then by used to control the parameters of stimulator(s) 150 in a closed-loop manner.

According to certain embodiments of the invention, the microstimulator causes tissue necrosis and consequent reduction in the volume of the prostate, thereby treating BPH. Direct electric current, and more particularly, relatively low-level direct electric current (e.g., between about 0.1 mA and about 10.0 mA) Is likely to produce such necrosis. (While tissue necrosis ultimately leads to reduction in volume of tissue, this therapy may cause short-term inflammation, edema, and/or swelling of the prostate, which may transiently Increase the volume of the prostate.)

According to various embodiments of the invention, the electrical stimulation provided by the microstimulator causes a reduction in the rate of growth of the prostate and a consequent reduction in the rate of volume expansion of the prostate, thereby treating BPH. Direct electric current, and more particularly, relatively low-level direct electric current (e.g., between about 0.1 mA and about 1.0 mA) is also likely to produce such a decrease in growth rate.

Furthermore, sensor(s) described earlier may be used to orchestrate first the activation of microstimulator(s) targeting one area of the prostate, and then, when appropriate, the microstimulator(s) targeting the same or another area of the prostate, in order to control symptoms, for instance, by a different means. Alternatively, this orchestration may be programmed, and not based on a sensed condition.

While the invention herein disclosed has been described by way of specific embodiments and applications thereof, numerous modifications and variations could be made thereto by those skilled in the art without departing from the scope of the invention set forth in the claims.

What is claimed is:

1. A method for treating a patient with BPH, comprising:
providing at least one stimulator having at least two electrodes;
implanting the at least one stimulator in the prostate;
providing operating power to the at least one stimulator;
providing stimulation parameters to the at least one stimulator;
generating direct electric current in accordance with the stimulation parameters; and
delivering the current to prostate tissue near the at least one stimulator;
wherein the at least one stimulator has a size and shape suitable for placement entirely within the prostate.

2. The method of claim 1 wherein the direct electric current is delivered at a relatively low level.

3. The method of claim 2 wherein the relatively low-level direct electric current is delivered at between about 0.1 mA and about 10.0 mA.

4. The method of claim 1 further comprising
providing at least one sensor;
using the at least one sensor to sense at least one physical condition; and
providing the stimulation parameters based at least in part upon the at least one sensed condition.

5. The method of claim 4 wherein the sensed physical condition includes at least one of tissue necrosis, tissue volume, pressure, oxygen level, impedance, neurotransmitter level, change in neurotransmitter level, pH level, pH level change, hormone level, hormone level change, PSA level, change in PSA level, enzyme level, change in enzyme level, interleukin level, change in interleukin level, cytokine level, change in cytokine level, lymphokine level, change in lymphokine level, chemokine level, change in chemokine level, growth factor level, change in growth factor level, neurotransmitter level, change in neurotransmitter level, ketone level, change in ketone level, electrolyte level, change in electrolyte level, medication level, medication level change, drug level, change in drug level, EMG, level of a blood-borne substance, change in the level of a blood-borne substance, level of a local interstitial fluid, and change in the level of a local interstitial fluid.

6. The method of claim 4 wherein the at least one sensor is a part of the stimulator.

7. The method of claim 1 wherein the at least one stimulator is leadless.

8. The method of claim 7 further comprising providing and implanting more than one stimulator.

9. A microstimulator for treating a patient with BPH, comprising:
electrical circuitry controlling electrical stimulation delivered to tissue;
at least two electrodes electrically connected to the electrical circuitry and configured to deliver the electrical stimulation to the prostate; and
wherein the microstimulator is configured for implantation entirely within or near the prostate.

10. The microstimulator of claim 9 wherein the electrical circuitry is configured to generate direct electric current to be delivered via the electrodes at between about 0.1 mA and about 1 mA.

11. The microstimulator of claim 9 wherein the microstimulator is substantially cylindrical-shaped.

12. The microstimulator of claim 9 wherein the microstimulator is substantially pancake-shaped.

13. The microstimulator of claim 9 wherein the microstimulator is substantially spherical-shaped.

14. The microstimulator of claim 9 further comprising at least one sensor for sensing at least one physical condition.

15. The microstimulator of claim 14 further configured to control stimulation at least in part according to the at least one sensed physical condition.

16. A method for treating a patient with BPH, comprising:
providing at least one stimulator having at least two electrodes;
implanting at least one electrode of the at least one stimulator in the prostate;
providing operating power to the at least one stimulator;
providing stimulation parameters to the at least one stimulator; and
delivering direct electric current in accordance with the stimulation parameters to prostate tissue near the at least two electrodes;
wherein the at least one stimulator has a size and shape suitable for placement entirely within or near the prostate.

17. The method of claim 16, further comprising:
providing at least one sensor;
using the sensor to sense a physical condition; and
determining the stimulation parameters based at least in part upon the sensed condition.

18. The method of claim 16 wherein the at least one sensor is a part of the stimulator.

19. The method of claim 16 wherein the stimulation parameters are determined using at least one external appliance.

20. The method of claim 16 wherein the stimulation parameters are determined by the at least one stimulator.

21. The method of claim 16 wherein the stimulation parameters are fixed.

22. The method of claim 16 wherein providing power to the at least one stimulator comprises receiving power from at least one external appliance.

23. The method of claim 22 wherein providing power to the at least one stimulator further comprises storing the power received from the at least one external appliance.

24. The method of claim 16 wherein the at least one stimulator is leadless.

25. The method of claim 16 further comprising providing and implanting more than one stimulator.

26. The method of claim 16 wherein the sensed physical condition includes at least one of tissue necrosis, tissue volume, pressure, oxygen level, impedance, neurotransmitter level, change in neurotransmitter level, pH level, pH level change, hormone level, hormone level change, PSA level, change in PSA level, enzyme level, change in enzyme level, interleukin level, change in interleukin level, cytokine level, change in cytokine level, lymphokine level, change in lymphokine level, chemokine level, change in chemokine level, growth factor level, change in growth factor level, neurotransmitter level, change in neurotransmitter level, ketone level, change in ketone level, electrolyte level, change in electrolyte level, medication level, medication level change, drug level, change in drug level, EMG, level of a blood-borne substance, change in the level of a blood-borne substance, level of a local interstitial fluid, and change in the level of a local interstitial fluid.

* * * * *